(12) United States Patent
Ma et al.

(10) Patent No.: US 10,054,503 B2
(45) Date of Patent: Aug. 21, 2018

(54) FORCE SENSOR

(71) Applicant: Microsoft Technology Licensing, LLC, Redmond, WA (US)

(72) Inventors: Siyuan Ma, Redmond, WA (US); James David Holbery, Bellevue, WA (US); Flavio Protasio Ribeiro, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/068,306

(22) Filed: Mar. 11, 2016

(65) Prior Publication Data
US 2017/0261388 A1 Sep. 14, 2017

(51) Int. Cl.
*G01L 1/04* (2006.01)
*G01L 1/22* (2006.01)
(Continued)

(52) U.S. Cl.
CPC .......... *G01L 1/2287* (2013.01); *G02B 27/017* (2013.01); *G06F 1/163* (2013.01);
(Continued)

(58) Field of Classification Search
CPC ................ G01L 1/2287; G02B 27/017; G02B 2027/0134; G06F 1/163; G06F 3/0414;
(Continued)

(56) References Cited

U.S. PATENT DOCUMENTS 5,948,990 A 9/1999 Hashida
6,360,615 B1 3/2002 Smela
(Continued)

FOREIGN PATENT DOCUMENTS

CN 102042888 A 5/2011
WO 03060449 A1 7/2003
(Continued)

OTHER PUBLICATIONS

Cotton, D. et al., "A Multifunctional Capacitive Sensor for Stretchable Electronic Skins," IEEE Sensors Journal, vol. 3, No. 12, Dec. 2009, Current Version Published Nov. 4, 2009, 2 pages.
(Continued)

*Primary Examiner* — Max Noori
(74) *Attorney, Agent, or Firm* — Alleman Hall Creasman & Tuttle LLP

(57) ABSTRACT

Examples of force sensors that may be incorporated into a number of devices or other objects are disclosed. In one example, a sensor includes a substrate including a first electrode and a second electrode, the first electrode and the second electrode being spaced by an insulating gap, and a compliant material with plural conductive pathways disposed over the gap and contacting the first electrode and the second electrode such that a resistance of an electrical path passing through the compliant material between the first electrode and the second electrode changes in response to force of the compliant material against one or more of the first electrode and the second electrode.

20 Claims, 10 Drawing Sheets

(51) Int. Cl.
*G06F 3/041* (2006.01)
*G06F 1/16* (2006.01)
*G02B 27/01* (2006.01)

(52) U.S. Cl.
CPC .......... *G06F 3/0414* (2013.01); *G06F 3/0416* (2013.01); *G02B 2027/0134* (2013.01); *G06F 2203/04102* (2013.01); *G06F 2203/04103* (2013.01); *G06F 2203/04105* (2013.01)

(58) Field of Classification Search
CPC ......... G06F 3/0416; G06F 2203/04102; G06F 2203/04103; G06F 2203/04105
USPC ...................... 73/862.381, 862.391, 862.632
See application file for complete search history.

(56) References Cited

U.S. PATENT DOCUMENTS

| | | | |
|---|---|---|---|
| 6,531,332 B1* | 3/2003 | Shkel | B81B 3/004 438/422 |
| 7,112,755 B2 | 9/2006 | Kitano et al. | |
| 7,343,807 B2 | 3/2008 | Lorenz | |
| 8,187,795 B2 | 3/2012 | Jain et al. | |
| 8,587,493 B2 | 11/2013 | Dickey et al. | |
| 8,800,386 B2* | 8/2014 | Taylor | G01L 1/18 73/862.041 |
| 9,116,570 B2 | 8/2015 | Lee et al. | |
| 9,336,761 B1* | 5/2016 | Marquez | G10H 1/0558 |
| 9,817,440 B2* | 11/2017 | Longinotti-Buitoni | G06F 1/163 |
| 2002/0121146 A1* | 9/2002 | Manaresi | B63H 9/06 73/862.68 |
| 2002/0123694 A1* | 9/2002 | Organ | A61B 5/0536 600/547 |
| 2002/0180578 A1* | 12/2002 | Sandbach | G06F 3/045 338/99 |
| 2005/0076824 A1 | 4/2005 | Cross et al. | |
| 2006/0046125 A1* | 3/2006 | Lai | H01M 8/0247 429/514 |
| 2006/0125033 A1* | 6/2006 | Segal | G01N 27/4146 257/415 |
| 2006/0175581 A1* | 8/2006 | Douglas | A41D 31/0066 252/500 |
| 2007/0000319 A1* | 1/2007 | Sasaki | G01F 23/268 73/301 |
| 2007/0103264 A1* | 5/2007 | Yang | H02N 1/004 335/220 |
| 2008/0238882 A1* | 10/2008 | Sivarajan | G06F 3/045 345/174 |
| 2009/0018428 A1* | 1/2009 | Dias | A41D 13/1281 600/388 |
| 2009/0020343 A1 | 1/2009 | Rothkopf et al. | |
| 2010/0033196 A1 | 2/2010 | Hayakawa et al. | |
| 2010/0051085 A1* | 3/2010 | Weidman | H01L 31/02244 136/244 |
| 2011/0057717 A1* | 3/2011 | Manning | B82Y 10/00 327/493 |
| 2011/0241704 A1* | 10/2011 | Laflamme | G01B 7/22 324/663 |
| 2012/0118066 A1 | 5/2012 | Majidi et al. | |
| 2012/0139864 A1 | 6/2012 | Sleeman et al. | |
| 2013/0082970 A1 | 4/2013 | Frey et al. | |
| 2013/0312541 A1 | 11/2013 | Majidi et al. | |
| 2013/0320467 A1 | 12/2013 | Buchanan et al. | |
| 2014/0238153 A1 | 8/2014 | Wood et al. | |
| 2014/0366650 A1 | 12/2014 | Thillainadarajah et al. | |
| 2015/0084909 A1 | 3/2015 | Worfolk et al. | |
| 2017/0176167 A1* | 6/2017 | Keller | G01B 7/18 |

FOREIGN PATENT DOCUMENTS

| | | |
|---|---|---|
| WO | 2007057321 A1 | 5/2007 |
| WO | 2011079390 A1 | 7/2011 |
| WO | 2011115403 A2 | 9/2011 |
| WO | 2014204323 A1 | 12/2014 |
| WO | 2015117125 A1 | 8/2015 |
| WO | 2015157272 A1 | 10/2015 |

OTHER PUBLICATIONS

Park, Y. et al., "Hyperelastic pressure sensing with a liquid-embedded elastomer," Journal of Micromechanics and Microengineering, vol. 20, No. 12, Dec. 2010, Published Online Nov. 29, 2010, 6 pages.
Wang, X. et al., "Transparent, stretchable, carbon-nanotube-inlaid conductors enabled by standard replication technology for capacitive pressure, strain and touch sensors," Journals of Materials Chemistry A, vol. 1, No. 11, Mar. 21, 2013, Published Online Jan. 25, 2013, 7 pages.
Hu, W. et al., "Elastomeric transparent capacitive sensors based on an interpenetrating composite of silver nanowires and polyurethane," Applied Physics Letters, vol. 102, No. 8, Feb. 25, 2013, 5 pages.
Fassler, A. et al., "Soft-matter capacitors and inductors for hyperelastic strain sensing and stretchable electronics," Smart Materials and Structures, vol. 22, No. 5, May 2013, Published Online Apr. 11, 2013, 8 pages.
Tabatabai, A. et al., "Liquid-Phase Gallium-Indium Alloy Electronics with Microcontact Printing," Langmuir, vol. 29, No. 20, May 21, 2013, Published Online Apr. 30, 2013, 7 pages.
Wissman, J. et al., "Soft-Matter Electronics with Stencil Lithography," Proceedings of IEEE Sensors 2013, Nov. 3, 2013, Baltimore, Maryland, 4 pages.
Yao, S. et al., "Wearable multifunctional sensors using printed stretchable conductors made of silver nanowires," Nanoscale, vol. 6, No. 4, Feb. 21, 2014, Published Online Dec. 5, 2013, 8 pages.
Choi, J. et al., "Improved Capacitive Pressure Sensors Based on Liquid Alloy and Silicone Elastomer," IEEE Sensors Journal, vol. 15, No. 8, Aug. 2015, Current Version Published Jun. 10, 2015, 2 pages.
Tai, Y. et al., "A highly sensitive, low-cost, wearable pressure sensor based on conductive hydrogel spheres," Nanoscale, vol. 7, No. 35, Sep. 21, 2015, Published Online Aug. 4, 2015, 8 pages.
"Customized Input Sensing—CIS Solutions", Published on: May 6, 2013 Available at: http://www.iee.lu/inoludes/content_jdm_framework/contenus/fichiers/el_2151_fichier_1/2013-05-06-CIS-Data-Sheet-web.pdf.
Gong, S. et al., "A Wearable and Highly Sensitive Pressure Sensor with Ultrathin Gold Nanowires", In Journal of Nature Communications, vol. 5, Feb. 4, 2014, 8 Pages.
ISA European Patent Office, International Search Report and Written Opinion Issued in PCT Application No. PCT/US2017/020556, dated Jun. 7, 2017, WIPO, 13 pages.
Vidal-Verdú, F. et al., "A Large Area Tactile Sensor Patch Based on Commercial Force Sensors", In Journal of Sensors, vol. 11, Iss. 5, May 19, 2011, 19 Pages.

* cited by examiner

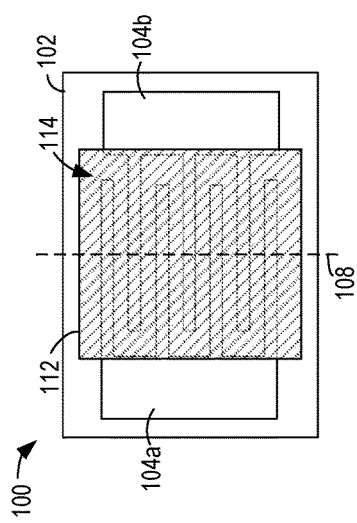
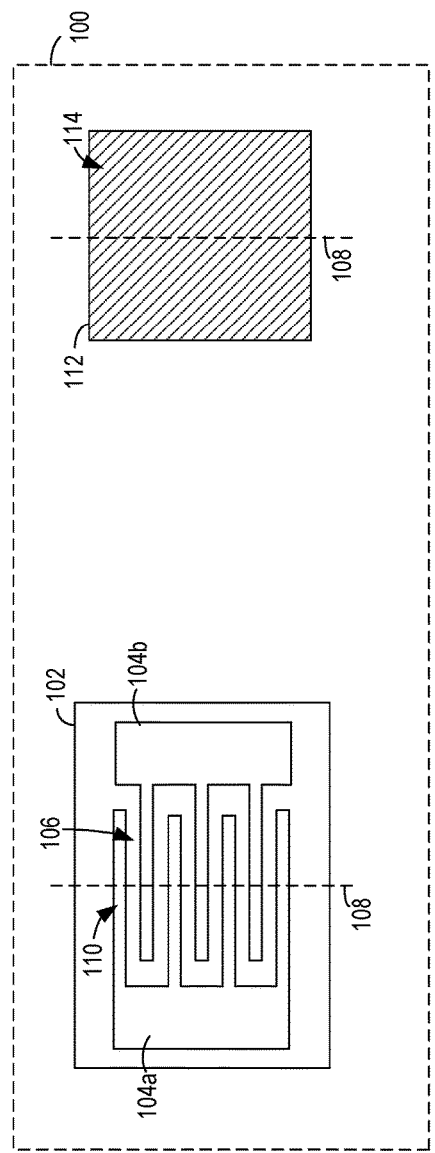

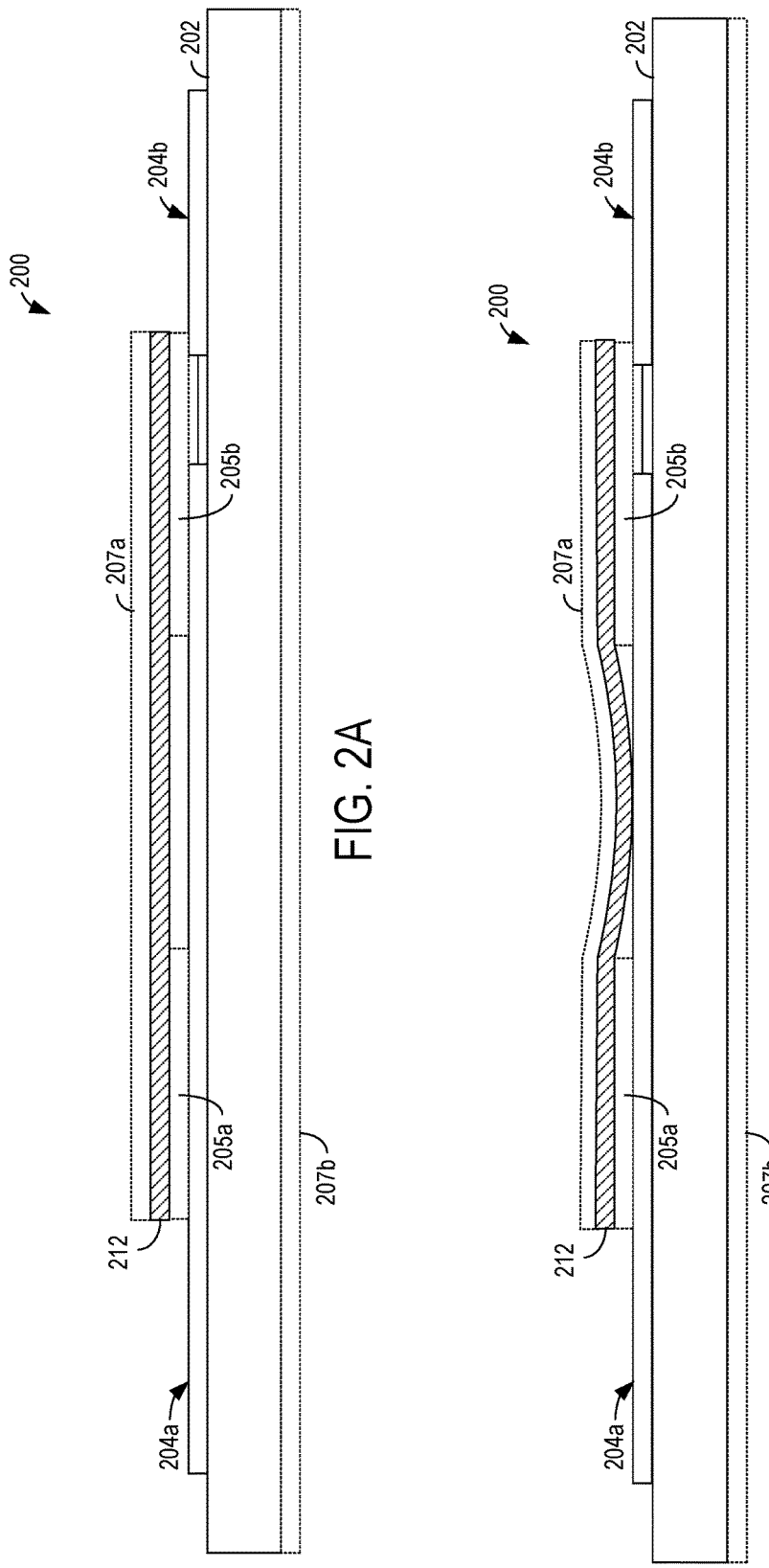

FORCE SENSOR

BACKGROUND

Force sensors may be utilized to measure changes in pressure and/or strain applied to the sensor. Such sensors may be used for a wide range of applications, including but not limited to providing input (user or environmental) to a computing device and measuring vibration experienced by an object.

SUMMARY

Examples related to force sensors are disclosed. In one example, a sensor comprises a substrate including a first electrode and a second electrode spaced by an insulating gap, and a compliant material with plural conductive pathways disposed over the gap and contacting the first electrode and the second electrode such that a resistance of an electrical path passing through the compliant material between the first electrode and the second electrode changes in response to force of the compliant material against one or more of the first electrode and the second electrode.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 1A shows a top view of an example force sensor, and FIG. 1B shows a view of the force sensor of FIG. 1A with a compliant material separated from first and second electrodes.

FIGS. 2A and 2B schematically show a side elevation view of an example force sensor as different amounts of force are applied to the sensor.

DETAILED DESCRIPTION

Figure 3:
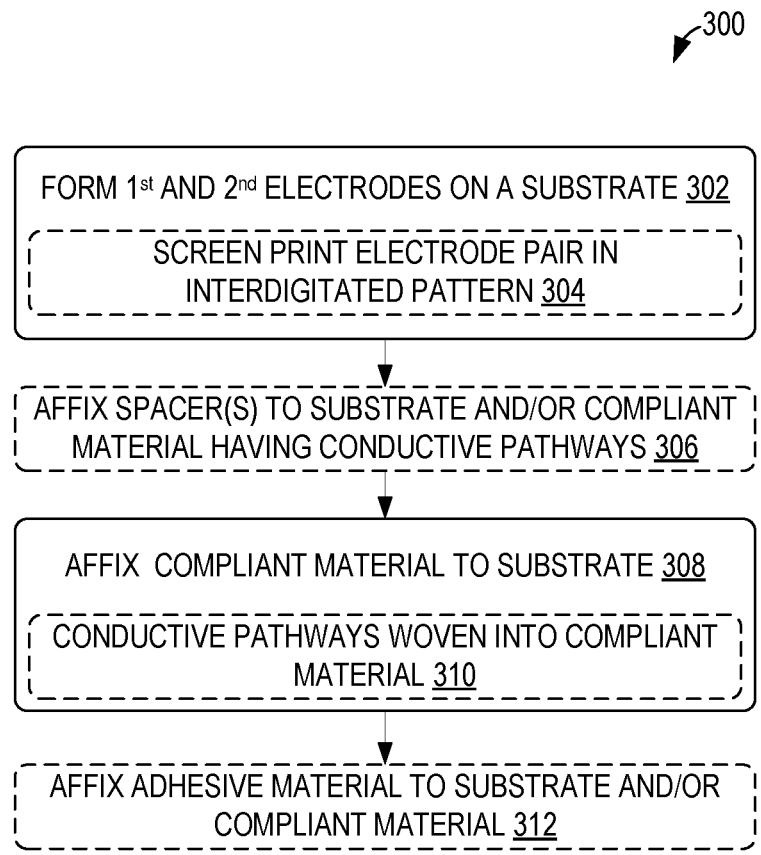
FIG. 3 is a flow chart illustrating an example method of manufacturing a force sensor.

Force sensors may be incorporated into a variety of devices, in order to provide touch input sensing, strain sensing, pressure sensing, and/or other sensing functions. These sensors may be relatively rigid, limiting the types of devices in which the sensors can be incorporated. Further, some sensors may be employed in rigid and/or electrically conductive environments, which may cause the sensors to have a low sensitivity to slight changes in force.

The present disclosure describes examples of force sensors that may have relatively higher sensitivities in such environments. Further, the disclosed examples may be formed from flexible materials, which may help to broaden a range of use environment for the disclosed sensors compared to more rigid force sensors. FIGS. 1A and 1B show a top view of an example force sensor 100, where FIG. 1A shows the sensor 100 in an assembled state, and FIG. 1B shows the sensor 100 in separated layers. A first layer (shown as a separate layer in FIG. 1B) comprises a substrate 102 including a first electrode 104a and a second electrode 104b. In the illustrated example, the first electrode 104a is interdigitated with the second electrode 104b to form an electrode pair. In other examples, the first electrode and the second electrode may form an electrode pair having any other suitable pattern. The substrate 102 may be rigid or flexible. The substrate 102 may be formed from any suitable non-conductive material, such as polyethylene terephthalate (PET) or other polymeric material.

The first and second electrodes 104a and 104b may formed in any suitable manner. In some examples, the electrodes may be printed (e.g., screen printed, ink jet printed, etc.) on the substrate. In another example, the electrodes may be formed via by depositing a conductor over an entirety of the substrate and then etching the electrode patterns. In yet other examples, a masking/deposition method (e.g. sputtering, evaporation, etc.) may be used to form the electrode pattern.

The first and second electrodes 104a and 104b may be formed from any suitable conductive material. For example, the first and second electrodes may be formed from silver, copper, aluminum, or other suitable metal. As illustrated in FIGS. 1A and 1B, the first and second electrodes are separated via an insulating gap 106 (e.g., air or a suitable dielectric material), and each comprises protruding fingers/prongs 110 portions that extend to form the interdigitated pattern. In this way, both electrodes intersect a central axis 108 of the sensor, such that protruding fingers/prongs 110 of the electrodes intersect at alternating locations along the central axis 108.

A second layer of the sensor 100 includes a compliant material 112 with plural conductive pathways 114. Any suitable materials may be used for the compliant material and conductive pathways. For example, the compliant material may comprise a fabric (e.g., an organic, synthetic, and/or blended fabric) with flexible conductive fibers/wires/nanowires woven or otherwise incorporated into the fabric as conductive pathways. The compliant material also may comprise an elastomeric sheet or other such non-fabric material. In yet other examples, the compliant material may comprise a composite of a fabric and a material coating or impregnating the fabric. The conductive pathways may include, but are not limited to, metallic wires, fibers coated with metallic materials, and conductive polymer fibers. The conductive pathways may form a regular pattern within all or a portion of the compliant material, may be distributed within the compliant material randomly, or incorporated in any other suitable manner.

As described in more detail below, the use of a flexible substrate and flexible compliant material/conductive pathways may allow the sensor to be incorporated into a wide variety of objects. For example, the compliant material may be integrated with and/or form at least a portion of an article of clothing, an upholstered object (e.g., furniture), a soft-touch housing for a handheld computing device or other electronic device (e.g. a fabric or elastomeric housing), a band for a wearable device, and/or other flexible/deformable material.

As shown in FIG. 1A, the sensor 100 includes the first layer (e.g., the substrate 102 and the electrodes 104a and 104b), with the second layer (e.g., the compliant material 112 with plural conductive pathways 114) disposed over the electrodes 104a and 104b. Thus, the plural conductive pathways 114 may come into a varying degree of contact with the electrodes based on an amount of force (e.g., which may include pressure and/or strain) applied to the compliant material 112 and/or substrate 102. As such, a resistance of an electrical path passing through the compliant material (e.g., the conductive pathways of the compliant material) between the first electrode and the second electrode may change based at least in part on an amount of force with which the compliant material and substrate are pressed together.

In some examples, as more force is applied to the sensor, more conductive pathways may come into contact with the electrodes 104a and 104b, bridging the electrode pair via a greater number of conductive paths and contacting the electrodes via a greater surface area. As such, the resistance of the electrical path between the electrode pair may decrease with an increase in such force, thereby allowing the detection of force.

A force sensor may include additional layers than those shown in FIGS. 1A and 1B. In some examples, a force sensor may include an adhesive layer applied to the substrate 102 and/or the compliant material 112 to facilitate attachment of the sensor to other objects. Where the force sensor is to be attached to a rigid object, an inelastic adhesive may be used to allow forces to be efficiently transferred to the sensor. Likewise, a more elastic adhesive may be used in other examples. In some examples, adhesives may be applied to both surfaces of a force sensor, for example, to couple the sensor to opposing structures at an interface between two structures for interfacial force measurement.

Further, a force sensor may include one or more spacers to separate at least a portion of the compliant material from the electrodes of the sensor. FIG. 2A illustrates an example force sensor 200 comprising adhesive layers and spacers. More particularly, sensor 200 comprises a substrate 202, and a first electrode 204a and a second electrode 204b forming an electrode pair on the substrate. A compliant material 212, including plural conductive pathways, is disposed over the electrodes 204a and 204b and spaced from the electrodes via spacers 205a and 205b. Conductive pathways in the compliant material are schematically represented by a diagonal hashing fill pattern. In other examples, such spacers may be omitted. FIG. 2A also shows example adhesive layers 207a and 207b disposed on an outer surface of the compliant material 212 and an outer surface of the substrate 202, respectively. As mentioned above, such adhesive layers are optional, and a sensor may be coupled to a surface for sensing in any other suitable manner.

In FIG. 2A, sensor 200 is illustrated in a first state in which the sensor is not subject to an applied force. As such, the compliant material is maintained out of contact with the electrodes via the spacers.

FIG. 2B illustrates sensor 200 in a second state, where a force has been applied to compliant material 212, bringing the compliant material (and one or more of the conductive pathways within the material) into contact with the electrodes 204a and 204b. In this way, an electrical path is formed between the electrode pair in such a manner that a resistance of the electrical path is a function of the force applied to the sensor 200.

FIG. 3 shows a flow chart for an example method 300 of manufacturing a force sensor. Method 300 may be used to manufacture sensors 100 and/or 200 of FIGS. 1 and 2A/2B, as examples. At 302, method 300 includes forming first and second electrodes on a substrate. As indicated at 304, the electrodes may be formed as pair in an interdigitated pattern. The electrodes may be formed in any suitable manner, such as by printing, patterned deposition, or etching of conductive material using lithographic techniques.

At 306, method 300 optionally includes affixing one or more spacers to the substrate, and/or a compliant material comprising conductive pathways as described above. At 308, method 300 further includes affixing the compliant material to the substrate (via optional spacers in some examples). As indicated at 310, the conductive pathways may be woven into the compliant material. For example, conductive fibers may be woven into a non-conductive fabric in order to manufacture the compliant material. In other examples, the conductive pathways may be incorporated into the compliant material in any other suitable manner.

Method 300 optionally includes affixing adhesive material to one or both of the substrate and the compliant material at 312. This may enable the sensor to be attached, removably or permanently, to an object for measuring force applied to that object. Depending upon the object to which the sensor is to be attached, the adhesive may be inelastic or elastic. In one more specific example, a non-elastic tape may be utilized as the adhesive material.

A force sensor according to the present disclosure may be incorporated into any suitable device or article. Examples include, but are not limited to, wearable computing devices such as head-mounted display devices, band devices, such as watches, flexible/stretchable articles such as fabric (e.g., in clothing, furniture, etc.), bandages, orthotics, etc., and handheld devices such as phones or tablet computers.

Figure 4:
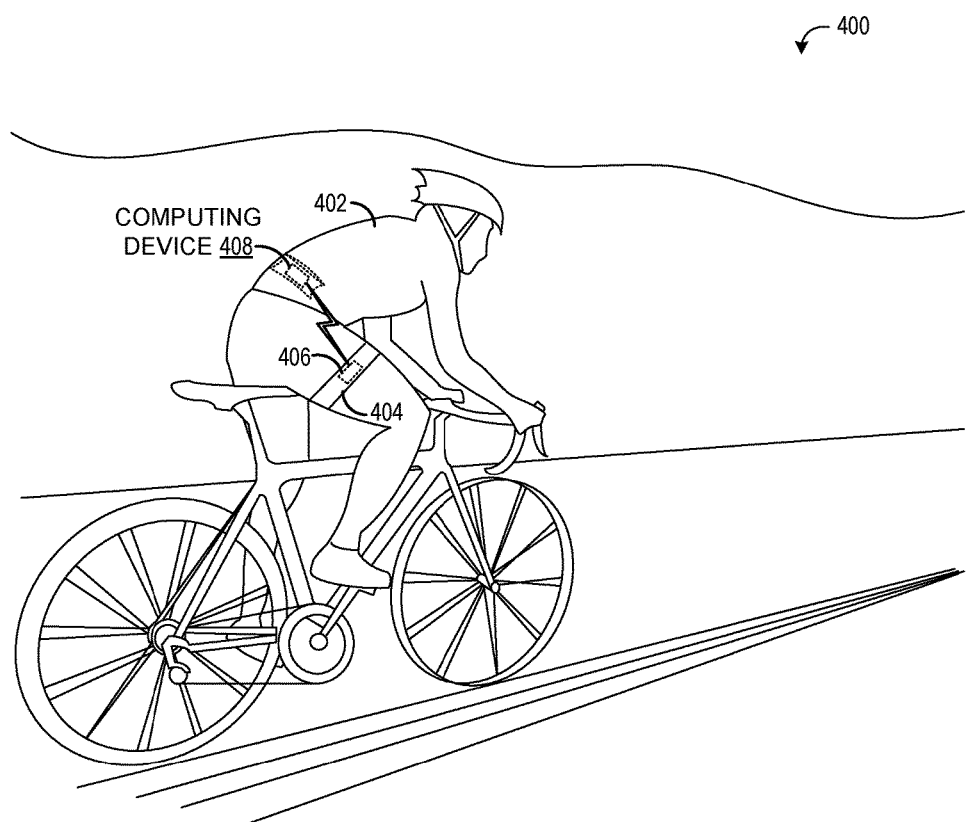
FIG. 4 shows an example stretchable article comprising an example force sensor.

FIG. 4 illustrates an example of a wearable article in the form of a band 404 including a force sensor 406, which is an example of sensor 100 of FIGS. 1A and 1B and sensor 200 of FIG. 2. Band 404 is configured to be worn around a body part of a user 402, for example around a leg of user 402 as shown in FIG. 4. Sensor 100 may be configured to detect force that may be induced by onset or recession of muscle swelling, muscle flexing, heartbeat, or other suitable body movement or function. Band 404 may be formed from any suitable material, including but not limited to fabrics and elastomeric materials. Sensor 406 may be mounted on an exterior of band 404, or may be incorporated into an interior of band 404. Sensor 406 may be configured to provide output to an operatively-coupled computing device 408 (e.g., a smartphone, activity tracker, or other device carried by the user 402) via a wired or wireless connection. Band 404 may take the form of a thin, belt-like strap, or a larger, sleeve-like enclosure.

Sensor 406 may output information usable by computing device 408 to monitor a condition of user 402, such as a level of muscle swelling, and notify user 402 and/or other users of the condition, for example to notify user 402 that his or her muscle is undergoing swelling so that user 402 can terminate his or her activity to prevent further injury. Similarly, such a sensor also may be used to monitor an injured muscle for recovery, e.g. by detecting a reduction in swelling of the injured muscle. In other examples, rather than be maintained in close contact with the leg of user 402 via band 404, sensor 406 may instead be incorporated into a pair of shorts, pants, shirt, socks, shoe, hat, or other article of clothing configured to have a suitably close fit to a body part.

Figure 5A:
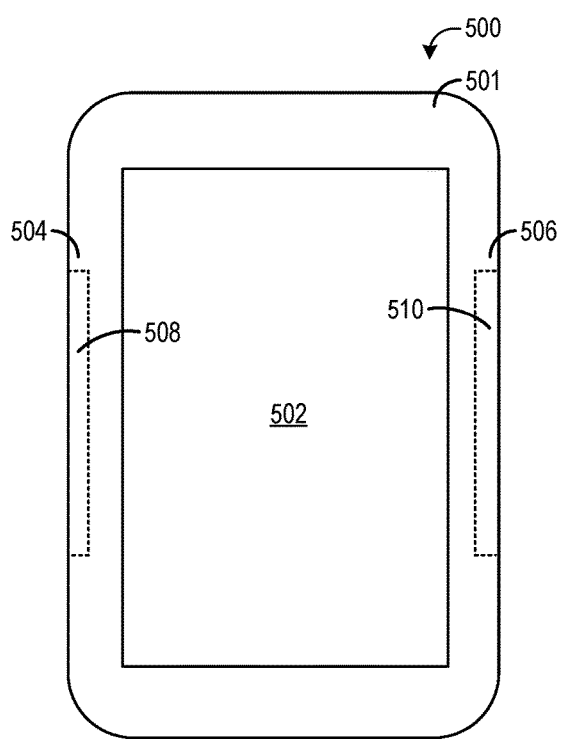
FIGS. 5A and 5B show an example device comprising an example force sensor.
Figure 5B:
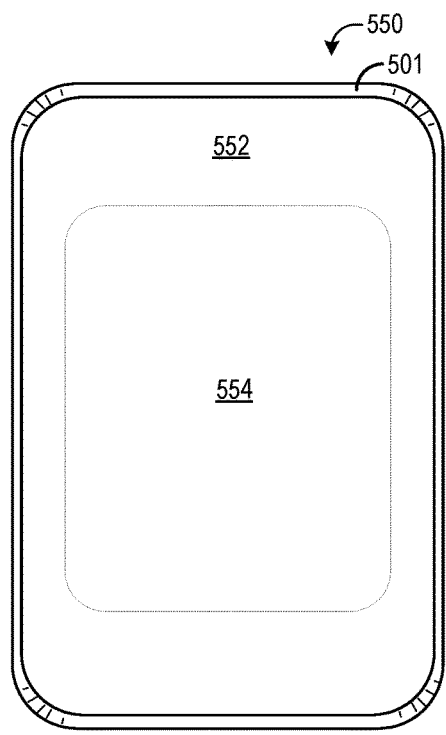

A sensor according to the present disclosure also may be incorporated into a computing device. FIGS. 5A and 5B illustrate an example of a hand-held computing device 501 in the form of a tablet computing device. FIG. 5A is a front view 500 of the hand-held computing device 501 and FIG. 5B is a back view 550 of the hand-held computing device 501. The hand-held computing device 501 may include a display 502 configured to display user interface controls, images, etc., responsive to instructions executed by a process of the hand-held computing device (not shown).

Various surfaces of the hand-held computing device 501 may be formed from a soft, deformable, and/or flexible material. For example, a first side surface 504 and second side surface 506 of the front of the hand-held computing device, as well as a back surface 552 of hand-held computing device 501, may be at least partially formed from a fabric, elastomeric, or other soft-feeling material. As such, one or more sensors as disclosed herein may be incorporated into one or more locations of the soft exterior surfaces. In the example of FIG. 5A, a first sensor 508 may be incorporated in the material of the first side surface 504 and a second sensor 510 may be incorporated in the material of second side surface 506. As shown in FIG. 5B, a third sensor 554 may be incorporated into the material of back surface 552. Sensor 100 of FIGS. 1A and 1B and sensor 200 of FIG. 2 are examples of sensors that may be used for each of first sensor 508, second sensor 510, and third sensor 554.

First sensor 508 and second sensor 510 may be configured to detect force applied to the first side surface 504 and second side surface 506 in order to measure a grip applied to hand-held computing device 501 when the device is held by a user. In such an example, force from a user's grip may be used for user interface interactions, e.g. to perform a selection operation in place of a mouse click or touch screen touch. Third sensor 554 may be configured to detect force-based inputs made to the back surface, for example. This may allow force-based user inputs to be made (e.g. by controlling a cursor or other suitable user interface mechanism) without having to release a grip of the hand-held computing device 501 to use a touch screen. It will be understood that hand-held computing device 501 may include a processor and storage comprising stored instructions executable by the processor to monitor the outputs of the sensors for such interactions, and to perform an action on the hand-held computing device responsive to a force-based input detected by one or more of the sensors. Example hardware configurations are described in more detail below.

Figure 9:
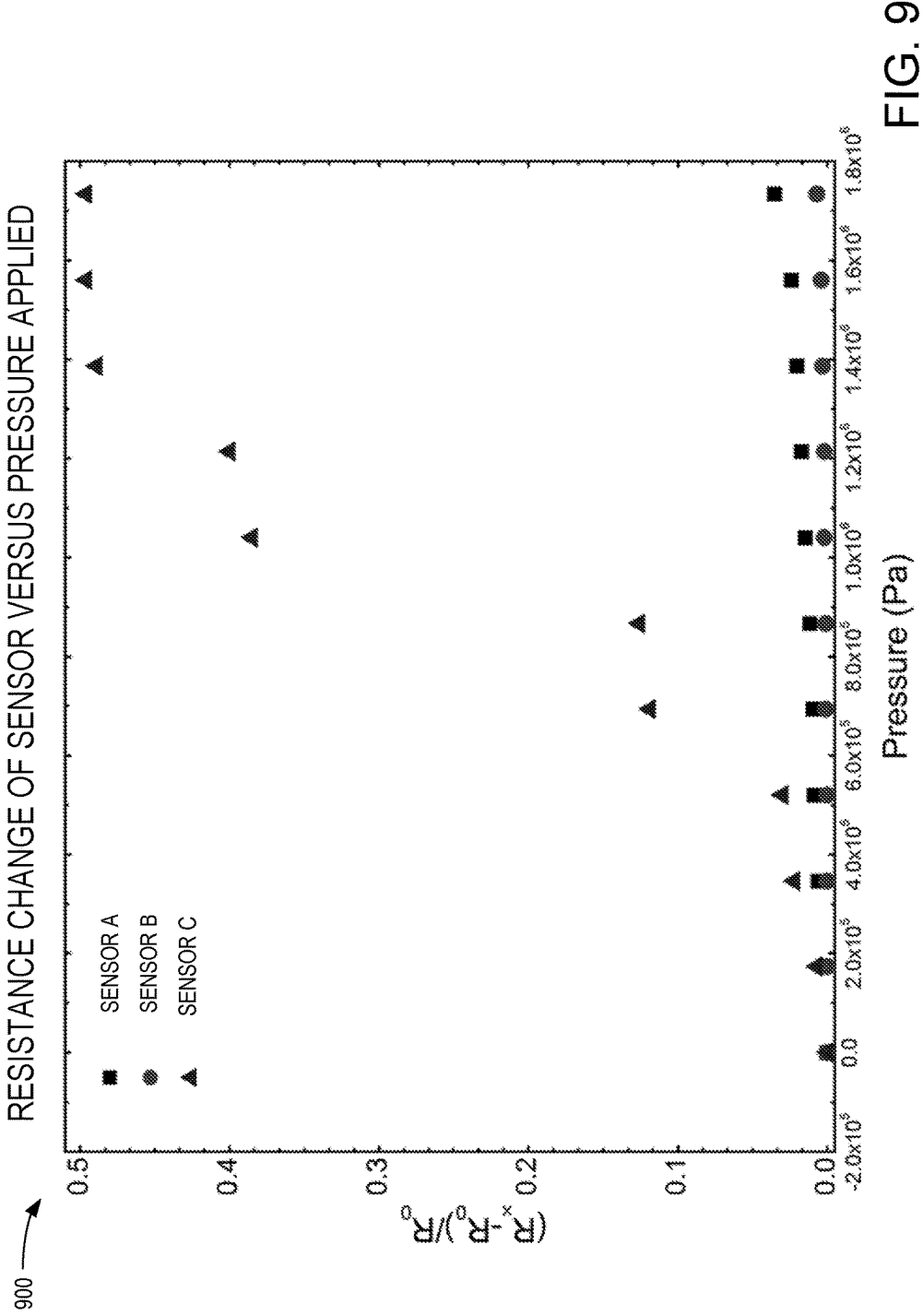
FIG. 9 shows a graph illustrating plots of observed resistance change versus pressure for an example force sensor according to the disclosure compared to other force sensors.

As the disclosed examples may have a relatively high sensitivity, they may provide a response to relatively light touches or presses. For example, FIG. 9 shows an example plot of normalized changes in resistance of an example sensor (sensor C) constructed according to the present disclosure compared to other commercially available sensors (sensors A and B). Sensor C was constructed of polyethylene terephthalate (PET) substrate (ST505, DuPont Teijin, available from E. I. du Pont de Nemours and Company of Wilmington, Del., USA), inkjet printed silver interdigitated electrode pair (silver nanoparticle ink printed with Fuji Dimatix inkjet printing system, available from Fujifilm Holdings Corporation of Minato, Tokyo, Japan), silver knit conductive fabric (available from Adafruit Industries, LLC, New York City, N.Y., USA), acrylic adhesive film as spacer structure (0.2 mm thickness, available from The 3M Company, Saint Paul, Minn., USA) and a protection tape as compliant material (PROTECRITE, available from American Biltrite Inc., Wellesley Hills, Mass., USA). Sensor A and sensor B were state-of-the-art commercially available sensors, which measured forces based on electron tunneling effect. Sensor A and B were constructed of polyimide (PI) substrate, patterned gold electrodes and gold nanoparticles with accurately-controlled inter-particle spacing. Differences in sensor behaviors of sensor A and B may be attributed to differences in gold nanoparticle properties and electrode structures. The plotted measurements were acquired by applying forces through a mechanical interface to the sensors, the mechanical interface being an aluminum panel having 2.5 mm thickness and 3 mm standoff distance. As illustrated, sensor C, has a higher sensitivity to most applied pressures shown on the graph.

Figure 6:
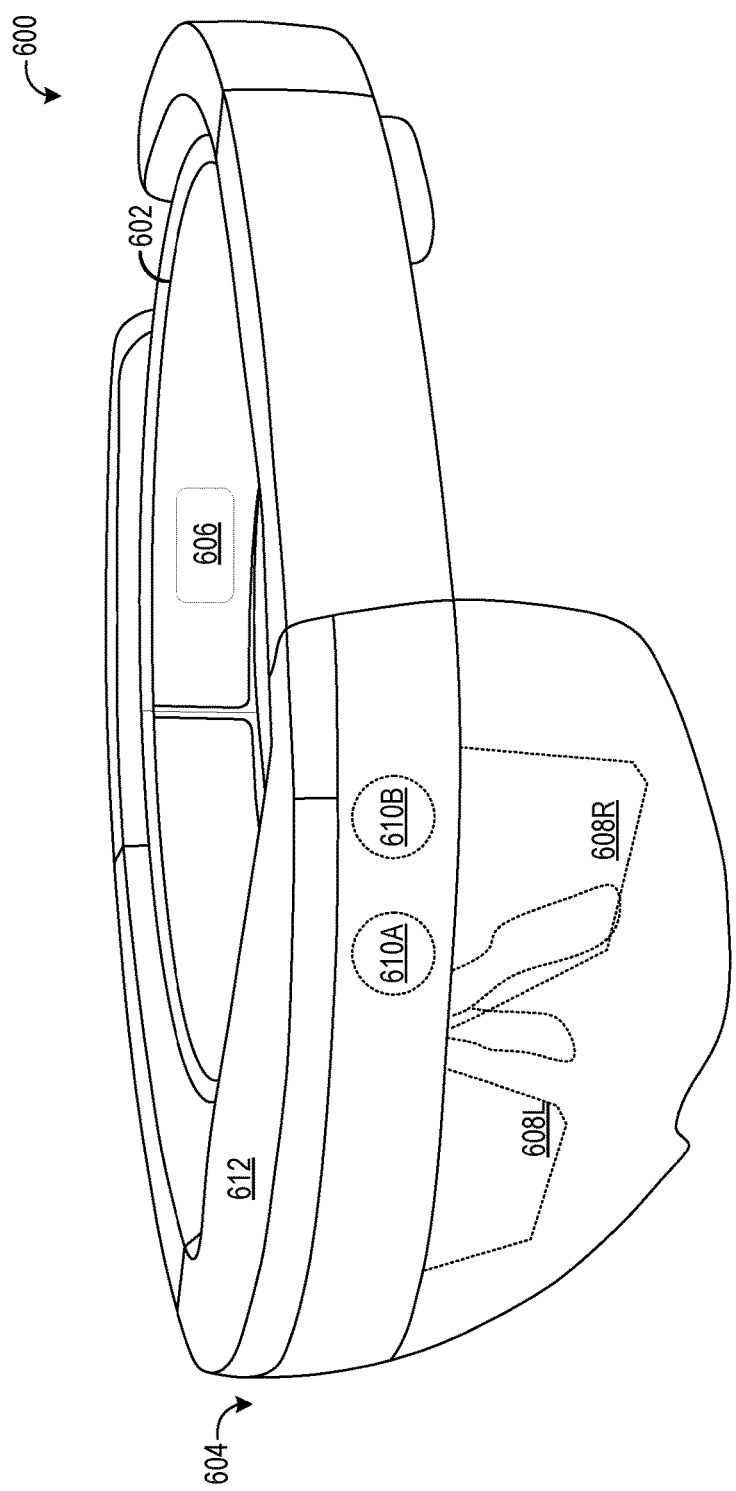
FIG. 6 shows another example device comprising an example force sensor.

FIG. 6 illustrates an example of a wearable computing device in the form of an example head-mounted display device (HMD) 600. The illustrated HMD includes an adjustable band 602 that supports componentry 604 of the HMD, including stereoscopic, see-through display componentry, configured to be positioned close to a user's eyes. Accordingly, the HMD may be used in augmented-reality applications, where real-world imagery is admixed with virtual display imagery. To increase comfort of a wearer of HMD 600, band 602 may be made of or include an outer layer of soft, deformable, and/or flexible material, such as fabric or an elastomeric material.

HMD 600 includes separate right and left display panels 608R/608L, cameras 610A/610B, and a controller 612. The controller is operatively coupled to the display panels, cameras, and other componentry. The controller includes logic and associated computer memory configured to provide image signal to the display panels, to receive video from the cameras, and to enact various control processes of the HMD. The controller may include a wired or wireless interface for exchanging data with a remote computer system, and/or receiving power from an external power source.

In order to maintain displayed images in desired registration with real-world objects, it may be desirable to maintain the display panels at a fixed location relative to a wearer's eyes, even as the wearer moves his or her head, thus dictating that adjustable band 602 be maintained in a relatively tight position around the head of the wearer. However, if band 602 is adjusted to a position that is too tight, force may be exerted against the wearer's head, leading to discomfort over time.

Thus, band 602 may include a force sensor 606 configured to detect a force exerted by band 602 against a wearers head. Sensor 100 of FIGS. 1A and 1B and sensor 200 of FIG. 2 are examples of sensors that may be used as force sensor 606. If the level of tension exceeds a designated level, controller 612 may be configured to output a notification (via the display panels, for example) instructing the wearer to loosen band 602. In other examples, if the level of tension is less than a second threshold, controller 612 may be configured to output a notification (via the display panels, for example) instructing the wearer to tighten band 602. It will be understood that HMD 600 is presented as an example of a wearable computing device, and that one or more sensors as disclosed herein may be used on any other suitable wearable computing device.

Figure 7:
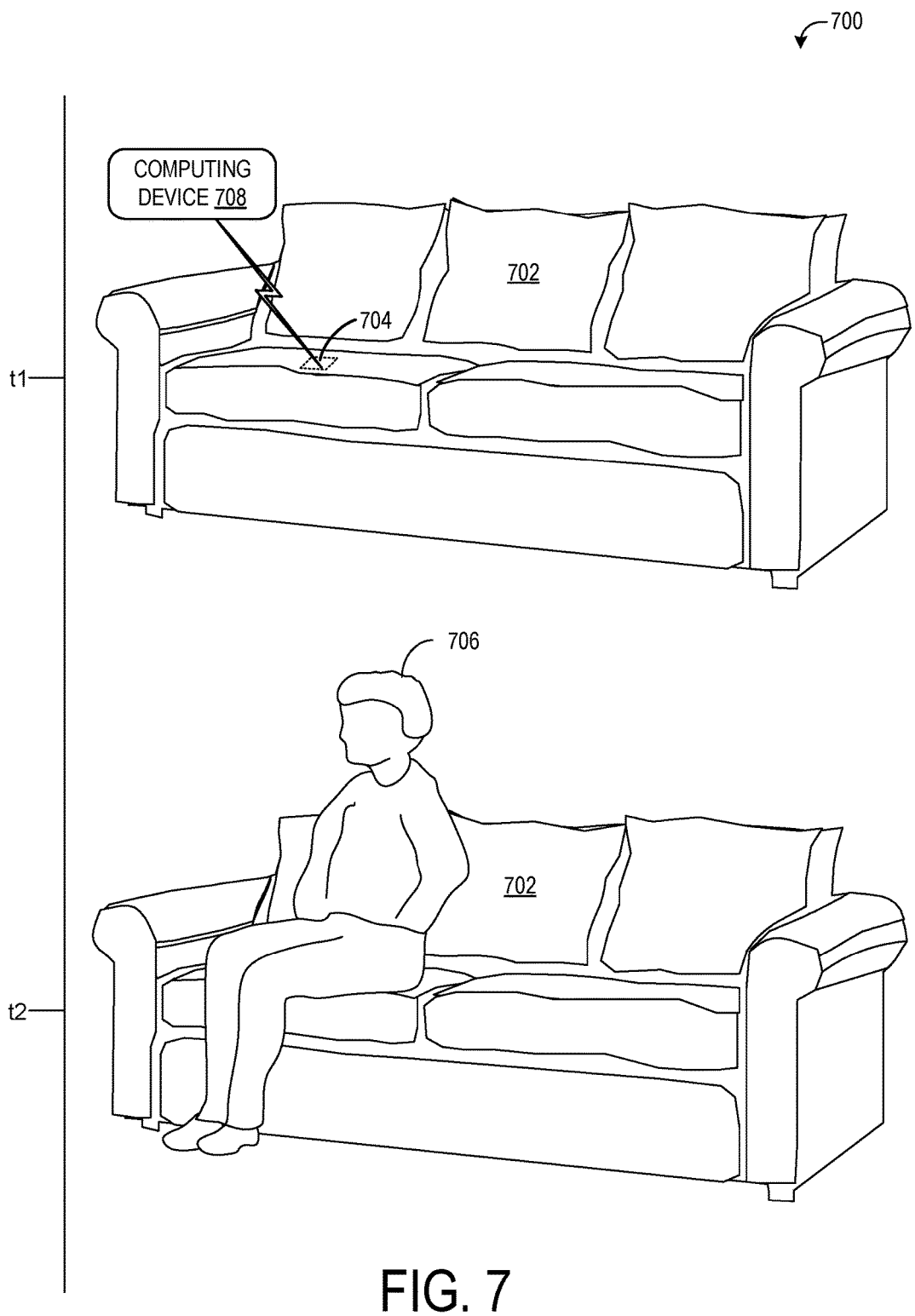
FIG. 7 shows another example article comprising an example force sensor.

FIG. 7 illustrates an example of an article in the form of a couch 702 including a force sensor 704. Sensor 100 of FIGS. 1A and 1B and sensor 200 of FIG. 2 are examples of sensor 704. Sensor 704 may be incorporated into the exterior surface of a cushion of couch 702. Specifically, FIG. 7 is a timeline 700 illustrating a user 706 applying force to the couch, as detected by sensor 704. At time t1, couch 702 is currently unused. As such, no force is detected by sensor 704. At time t2, user 706 sits on the cushion including sensor 704. As a result, sensor 704 detects the force placed on the couch by user 706. Sensor 704 may be operatively coupled to a computing device 708 via a wired or wireless connection. Computing device 708 may be a suitable device, such as a wearable computing device of user 706, a home entertainment system, and/or other suitable device. The output from sensor 704 may be used by computing device 708 to detect that user 706 is sitting on couch 702, for example. By detecting that user 706 is sitting on couch 702, various actions may be taken, including but not limited to automatically activating a display device (e.g., television) located in the environment or notifying user 706 when he or she has sat for a threshold duration, in order to encourage user 706 to stand up. Further, sensor 704 may be incorporated into other suitable devices or articles, including but not limited to car seats (e.g., in order to detect presence of a passenger in a seat), cribs, beds, and the like.

Figure 10:
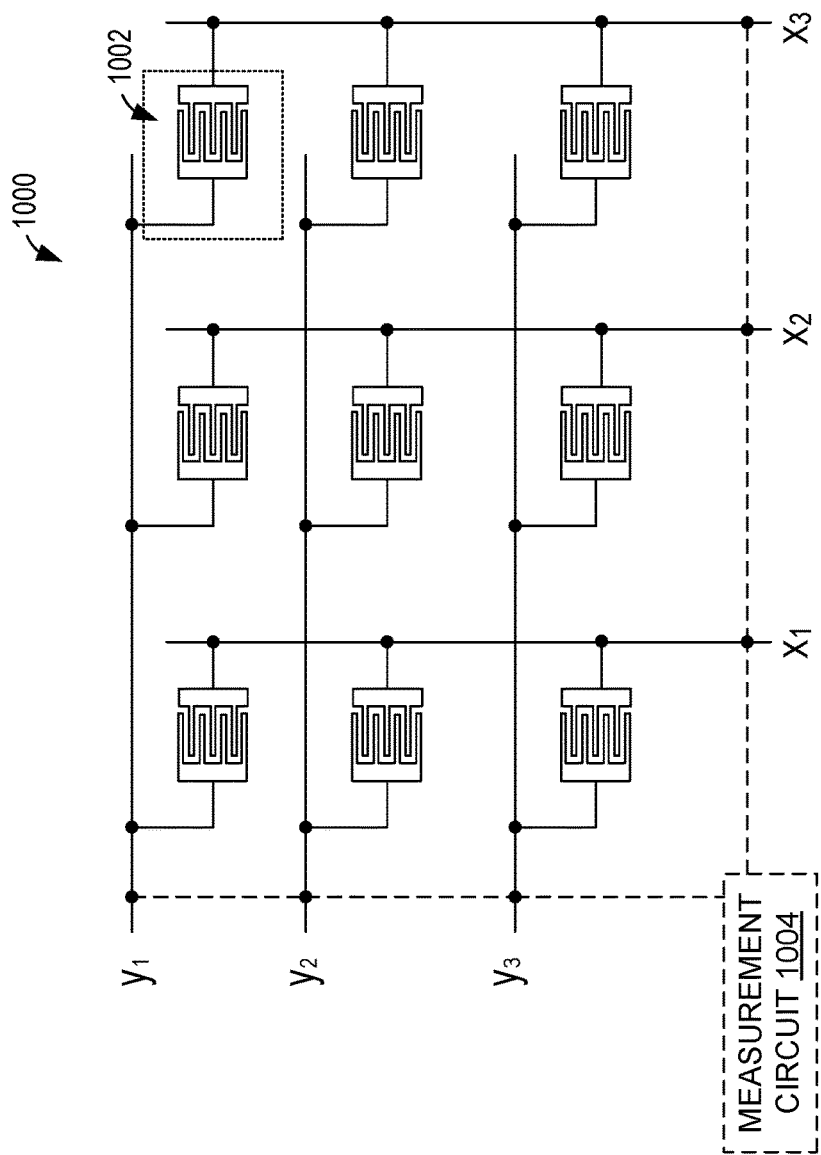
FIG. 10 schematically shows an example force sensor array.

FIG. 10 shows an example schematic diagram depicting an example sensor array 1000 comprising a plurality of force sensors 1002 arranged in a grid formation. Sensor 100 of FIGS. 1A and 1B and sensor 200 of FIG. 2 are examples of sensors that may be used as one or more of force sensors 1002. The arrangement of multiple force sensors in a grid may be useful for two-dimensional force sensing applications. Although an example arrangement is illustrated in FIG. 10, any suitable arrangement of multiple sensors in communication with one another and/or an intermediate computing device/communication bus may be used to provide the array of force sensors. The array 1000 may be coupled to a measurement circuit 1004 to measure resistance between any column $x_i$ and any row $y_j$, where i and j each range in value from 1 to 3 (in the illustrated example; in other examples, i and j may range in value based on the number of rows/columns of sensors, respectively). In other examples, any different indexing and/or measurement arrangement may be used.

In some embodiments, the methods and processes described herein may be tied to a computing system of one or more computing devices. In particular, such methods and processes may be implemented as a computer-application program or service, an application-programming interface (API), a library, and/or other computer-program product.

Figure 8:
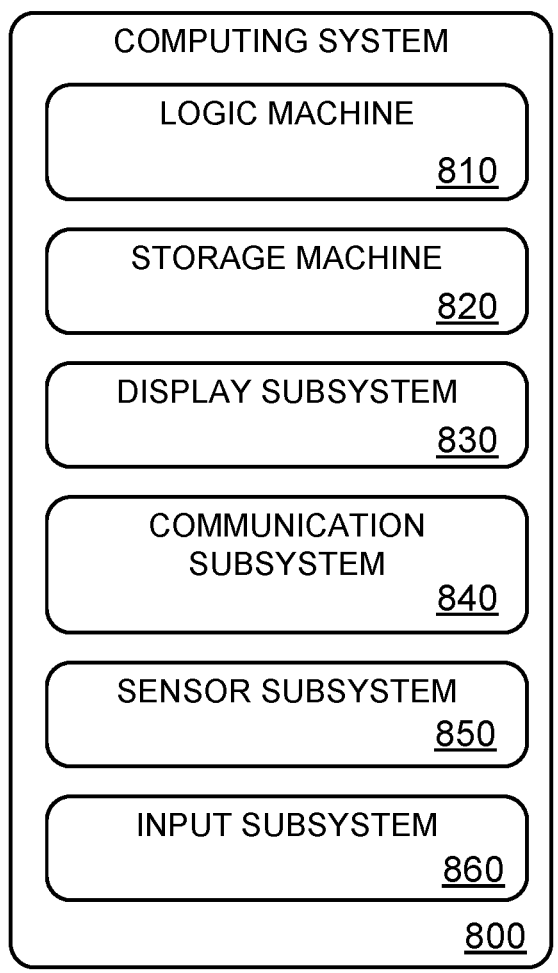
FIG. 8 schematically shows an example computing device.

FIG. 8 schematically shows a non-limiting embodiment of a computing system 800 that may enact one or more of the methods and processes described above. Computing system 800 is shown in simplified form. Computing system 800 may take the form of one or more personal computers, server computers, tablet computers, home-entertainment computers, network computing devices, gaming devices, mobile computing devices, mobile communication devices (e.g., smart phone), and/or other computing devices. Computing system 800 is a non-limiting example of computing device 408, hand-held computing device 501, HMD 600, and/or computing device 708 described above with respect to FIGS. 4-7, respectively. Further, local and/or remote computing systems configured to receive output from the force sensor of the disclosure may also be non-limiting examples of computing system 800.

Computing system 800 includes a logic machine 810 and a storage machine 820. Computing system 800 may optionally include a display subsystem 830, input subsystem 860, communication subsystem 840, sensor subsystem 850, and/or other components not shown in FIG. 8.

Logic machine 810 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 820 includes one or more physical devices configured to hold instructions executable by the logic machine to implement the methods and processes described herein. When such methods and processes are implemented, the state of storage machine 820 may be transformed—e.g., to hold different data.

Storage machine 820 may include removable and/or built-in devices. Storage machine 820 may include optical memory (e.g., CD, DVD, HD-DVD, Blu-Ray Disc, etc.), semiconductor memory (e.g., RAM. EPROM, EEPROM, etc.), and/or magnetic memory (e.g., hard-disk drive, floppy-disk drive, tape drive, MRAM, etc.), among others. Storage machine 820 may include volatile, nonvolatile, dynamic, static, read/write, read-only, random-access, sequential-access, location-addressable, file-addressable, and/or content-addressable devices.

It will be appreciated that storage machine 820 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 810 and storage machine 820 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 830 may be used to present a visual representation of data held by storage machine 820. This visual representation may take the form of a graphical user interface (GUI). As the herein described methods and processes change the data held by the storage machine, and thus transform the state of the storage machine, the state of display subsystem 830 may likewise be transformed to visually represent changes in the underlying data. Display subsystem 830 may include one or more display devices utilizing virtually any type of technology. Such display devices may be combined with logic machine 810 and/or storage machine 820 in a shared enclosure, or such display devices may be peripheral display devices.

When included, input subsystem 860 may comprise or interface with one or more user-input devices such as a keyboard, mouse, touch screen, or game controller. In some embodiments, the input subsystem may comprise or interface with selected sensors of sensor subsystem 850, such as natural user input (NUI) componentry. Such componentry may be integrated or peripheral, and the transduction and/or processing of input actions may be handled on- or off-board. Example NUI componentry included in sensor subsystem 850 may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Sensor subsystem 850 may include one or more force sensors, such as sensor 100 or sensor 200 described above with respect to FIGS. 1 and 2, respectively.

When included, communication subsystem 840 may be configured to communicatively couple computing system 800 with one or more other computing devices. Communication subsystem 840 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 800 to send and/or receive messages to and/or from other devices via a network such as the Internet.

Another example provides for a sensor comprising a substrate comprising a first electrode and a second electrode, the first electrode and the second electrode being spaced by an insulating gap, and a compliant material with plural conductive pathways disposed over the gap and contacting the first electrode and the second electrode such that a resistance of an electrical path passing through the compliant material between the first electrode and the second electrode changes in response to force of the compliant material against one or more of the first electrode and the second electrode. Such an example may additionally or alternatively further include the sensor wherein the first electrode is interdigitated with the second electrode. Such an example may additionally or alternatively include the sensor wherein the substrate comprises a flexible material. Such an example may additionally or alternatively include the sensor wherein the first electrode and the second electrode are printed on the substrate. Such an example may additionally or alternatively include the sensor wherein the compliant material comprises fabric and the plural conductive pathways comprise conductive fibers woven into the fabric. Such an example may additionally or alternatively include the sensor wherein the compliant material comprises one or more of an upholstered object and an article of clothing. Such an example may additionally or alternatively include the sensor wherein the compliant material forms at least a portion of a housing of an electronic device. Such an example may additionally or alternatively include the sensor wherein the first electrode and the second electrode form an electrode pair, the sensor further comprising a spacer positioned between the electrode pair and at least a portion of the compliant material. Such an example may additionally or alternatively include the sensor further comprising an adhesive material for adhering the sensor to a surface. Any or all of the above-described examples may be combined in any suitable manner in various implementations.

Another example provides for a sensor comprising a substrate comprising a first electrode and a second electrode, the first electrode and the second electrode being spaced by an insulating gap, and a fabric disposed over the gap, the fabric material having plural conductive pathways woven into the fabric and contacting the first electrode and the second electrode such that a resistance of an electrical path passing through the fabric material between the first electrode and the second electrode changes in response to force of the fabric material against one or more of the first electrode and the second electrode. Such an example may additionally or alternatively include the sensor wherein the first electrode is interdigitated with the second electrode. Such an example may additionally or alternatively include the sensor wherein the substrate is flexible. Such an example may additionally or alternatively include the sensor wherein the first electrode and the second electrode are screen printed on the substrate. Such an example may additionally or alternatively include the sensor wherein the compliant material is included in one or more of an article of clothing, an upholstered object, a band for a wearable device, and at least a portion of a housing of an electronic device. Any or all of the above-described examples may be combined in any suitable manner in various implementations.

Another example provides for a method of manufacturing a sensor, the method comprising forming a first electrode and a second electrode on a substrate, the first electrode and the second electrode being spaced by an insulating gap, and affixing a compliant material including plural conductive pathways to the substrate such that the plural conductive pathways are disposed over the gap and contact the first electrode and the second electrode to form an electrical path passing through the compliant material between the first electrode and the second electrode, and such that a resistance of the electrical path changes in response to force of the compliant material against one or more of the first electrode and the second electrode, the plural conductive pathways being woven into the compliant material. Such an example may additionally or alternatively include the method wherein forming the first electrode and the second electrode on the substrate comprises screen printing the first electrode and the second electrode in an interdigitated pattern on the substrate. Such an example may additionally or alternatively include the method wherein the substrate comprises a flexible material. Such an example may additionally or alternatively include the method wherein the plural conductive pathways comprise a plurality of flexible conductive wires that are woven into fabric of one or more of an article of clothing, an upholstered object, a band for a wearable device, and at least a portion of a housing of an electronic device. Such an example may additionally or alternatively include the method wherein the first electrode and the second electrode form an electrode pair, the method further comprising affixing one or more non-conductive spacers to one or more of the electrode pair, the substrate, and the compliant material, the one or more non-conductive spacers separating at least a portion of the electrode pair from at least a portion of the plural conductive pathways. Such an example may additionally or alternatively include the method further comprising affixing an adhesive material to one or more of the substrate and the compliant material. Any or all of the above-described examples may be combined in any suitable manner in various implementations.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A sensor comprising:
    a substrate comprising a first electrode and a second electrode, the first electrode and the second electrode being spaced by an insulating gap;
    a spacer disposed adjacent to the first electrode and the second electrode; and
    a compliant fabric material with plural conductive pathways disposed over the insulating gap, at least a portion of the compliant fabric material separated from the first electrode and the second electrode by the spacer such that an electrical path passes through the compliant fabric material between the first electrode and the second electrode when the compliant fabric material is moved to contact the first electrode and the second electrode and a resistance of the electrical path changes in response to a force of the compliant fabric material against one or more of the first electrode and the second electrode.

2. The sensor of claim 1, wherein the first electrode is interdigitated with the second electrode.

3. The sensor of claim 1, wherein the substrate comprises a flexible material.

4. The sensor of claim 1, wherein the first electrode and the second electrode are printed on the substrate.

5. The sensor of claim 1, wherein the plural conductive pathways comprise conductive fibers woven into fabric.

6. The sensor of claim 1, wherein the compliant fabric material comprises one or more of an upholstered object and an article of clothing.

7. The sensor of claim 1, wherein the compliant fabric material forms at least a portion of a housing of an electronic device.

8. The sensor of claim 1, wherein the first electrode and the second electrode form an electrode pair, and wherein the spacer is positioned between the electrode pair and at least the portion of the compliant fabric material.

9. The sensor of claim 1, further comprising an adhesive material for adhering the sensor to a surface.

10. A sensor comprising:
    a substrate comprising a first electrode and a second electrode, the first electrode and the second electrode being formed on a same surface of the substrate and being spaced by an insulating gap;
    a spacer disposed adjacent to the first electrode and the second electrode; and
    a fabric material disposed over the insulating gap, the fabric material having plural conductive pathways woven into the fabric material and at least a portion of the fabric material being separated from the first electrode and the second electrode by the spacer such that an electrical path passes through the fabric material between the first electrode and the second electrode when the fabric material is moved to contact the first electrode and the second electrode and a resistance of the electrical path changes in response to a force of the fabric material against one or more of the first electrode and the second electrode.

11. The sensor of claim 10, wherein the first electrode is interdigitated with the second electrode.

12. The sensor of claim 10, wherein the substrate is flexible.

13. The sensor of claim 10, wherein the first electrode and the second electrode are screen printed on the substrate.

14. The sensor of claim 10, wherein the fabric material is included in one or more of an article of clothing, an upholstered object, a band for a wearable device, and at least a portion of a housing of an electronic device.

15. A method of manufacturing a sensor, the method comprising:
    forming a first electrode and a second electrode on a same surface of a substrate, the first electrode and the second electrode being spaced by an insulating gap;
    affixing a spacer adjacent to the first electrode and the second electrode; and
    affixing a compliant fabric material including plural conductive pathways to the spacer such that the plural conductive pathways are disposed over the insulating gap and at least partially separated from the first electrode and the second electrode by the spacer, such that an electrical path passes through the compliant fabric material between the first electrode and the second electrode when the compliant fabric material is moved to contact the first electrode and the second electrode and a resistance of the electrical path changes in response to a force of the compliant fabric material against one or more of the first electrode and the second electrode, the plural conductive pathways being woven into the compliant fabric material.

16. The method of claim 15, wherein forming the first electrode and the second electrode on the substrate comprises screen printing the first electrode and the second electrode in an interdigitated pattern on the substrate.

17. The method of claim 15, wherein the substrate comprises a flexible material.

18. The method of claim 15, wherein the plural conductive pathways comprise a plurality of flexible conductive wires that are woven into fabric of one or more of an article of clothing, an upholstered object, a band for a wearable device, and at least a portion of a housing of an electronic device.

19. The method of claim 15, wherein the first electrode and the second electrode form an electrode pair, and wherein affixing the spacer comprises affixing one or more non-conductive spacers to one or more of the electrode pair, the substrate, and the compliant fabric material, the one or more non-conductive spacers separating at least a portion of the electrode pair from at least a portion of the plural conductive pathways.

20. The method of claim 15, further comprising affixing an adhesive material to one or more of the substrate and the compliant fabric material.

* * * * *